US00PP33459P3

(12) United States Plant Patent
Holtkamp, Jr. et al.

(10) Patent No.: US PP33,459 P3
(45) Date of Patent: Sep. 7, 2021

(54) AFRICAN VIOLET PLANT NAMED 'OP10664'

(50) Latin Name: *Saintpaulia ionantha*
Varietal Denomination: OP10664

(71) Applicant: HERMANN HOLTKAMP GREENHOUSES, INC., Nashville, TN (US)

(72) Inventors: Reinhold Holtkamp, Jr., Brentwood, TN (US); Martin Holtkamp, Isselburg-Vehlingen (DE)

( * ) Notice: Subject to any disclaimer, the term of this patent is extended or adjusted under 35 U.S.C. 154(b) by 0 days.

(21) Appl. No.: 16/501,964

(22) Filed: Jul. 12, 2019

(65) Prior Publication Data

US 2020/0022295 P1 Jan. 16, 2020

Related U.S. Application Data

(60) Provisional application No. 62/697,792, filed on Jul. 13, 2018.

(51) Int. Cl.
*A01H 5/02* (2018.01)
*A01H 6/44* (2018.01)

(52) U.S. Cl.
USPC ..... Plt./270
CPC ..... *A01H 6/444* (2018.05)

(58) Field of Classification Search
USPC ..... Plt./264, 270
See application file for complete search history.

(56) References Cited

PUBLICATIONS

UPOV-PLUTO: Plant Variety Database—updated on Mar. 14, 2020, for citation 'Gorgeous' (1 page total).*

* cited by examiner

*Primary Examiner* — Susan McCormick Ewoldt
(74) *Attorney, Agent, or Firm* — Foley & Lardner LLP

(57) ABSTRACT

A new and distinct cultivar of African Violet named 'OP10664' particularly characterized by its filantherless single, violet-shaped, bi-color purple flowers with a white center and occasional additional 1-3 small petals, upright flower stems that curve slightly toward the center to form a compact flower bouquet above the leaves; medium green, round to oval shaped leaves; vigorous and medium growth habit; flowering 9-10 weeks after potting, and very long-lasting and non-dropping flowers.

3 Drawing Sheets

Latin name: *Saintpaulia ionantha.*
Varietal denomination: 'OP10664'.

BACKGROUND OF THE INVENTION

The present invention comprises a new and distinct cultivar of African Violet plant, botanically known as *Saintpaulia ionantha*, and hereinafter referred to by the cultivar name 'OP10664'.

The new cultivar was referred to during the breeding and selection process by the designation '5050 bl w KS 15' and is a product of a planned breeding program. The new cultivar originated from a cross made by the inventors, Martin Holtkamp and Reinhold Holtkamp in the controlled breeding program in Isselburg, Germany. The female, or seed parent was a cultivar designated '5027/20 Flied' The male, or pollen parent was a cultivar designated '5027/hbl KS*'.

'OP10664' was discovered and selected by the inventors as a flowering plant within the progeny of the stated cross in a controlled environment in Isselburg, Germany. Asexual reproduction of the new cultivar by leaf cuttings, as performed by the grower Reinhold Holtkamp in Nashville, Tenn., has demonstrated that the combination of characteristics as herein disclosed for the new cultivar are firmly fixed and retained through successive generations of asexual reproduction. The new cultivar reproduces true-to-type.

'OP10664' has not been observed under all possible environmental conditions. The phenotype may vary significantly with variations in environment such as temperature, light intensity and day length without any change in genotype. The following observations, measurements and values describe the new cultivar as grown in Nashville, Tenn. and Isselburg, Germany under greenhouse conditions which closely approximate those generally used in commercial practice.

BRIEF SUMMARY OF THE INVENTION

The following characteristics have been repeatedly observed and are determined to be basic characteristics of 'OP10664', which in combination distinguish this African Violet as a new and distinct cultivar:

1) filantherless characteristic as described in plant patent application "Filantherless" characteristic. The characteristic of where the flower lacks the male reproductive parts of the filament and anther also known as the Stamen.
2) a single crown as large as 20-25 cm in diameter;
3) strong, upright flower stems curving slightly toward the center;
4) single violet-shaped, filantherless (characteristic lacking stamens: filaments and yellow anthers) bi-color purplish blue flower with white center and additional 1-3 small petals giving it a slightly wavy look.
5) each plant carries 8-12 upright flower stems each of which carries 10-14 flowers;

6) very long-lasting, non-dropping flowers; flowers last longer than standard violets that have the filaments and anthers still attached;
7) vigorous and compact growth;
8) plant saleable 12-13 weeks after potting;
9) medium green, plain leaves; and
10) after maturity the flowers dry off, and remain on the peduncle without becoming infected by *Botrytis*.

The new cultivar displays the filanterhless trait and has the white center with large colored edge. 'OP10664' has a wide purplish blue flower with a white center and somewhat larger blooms.

Plants of the new African Violet 'OP10664' differ from plants of the female or seed parent, the unpatented African Violet designated '5027/20 Flied', and the male parent, the unpatented African Violet designated '5027/hbl KS*', in the following characteristics described in Table 1:

TABLE 1

| Characteristic | New variety 'OP10664' | Female parent '5027/20 Flied' (unpatented) | Male parent '5027/hbl KS*' (unpatented) |
|---|---|---|---|
| Plant height | 12 to 15 cm | 10 to 12 cm | 10 to 13 cm |
| Number of flowers per inflorescence | 10 to 14 | 8 to 10 | 8 to 12 |
| Filantherless trait | More filantherless flowers than parent | At least one mature flower is absent of a stamen in the flower | At least one mature flower is absent of a stamen in the flower |

The major difference between 'OP10664' and other known African Violet cultivars is the lack of having a filament or an anther.

BRIEF DESCRIPTION OF THE DRAWINGS

The accompanying color photographic drawings show a typical specimen plant of the new cultivar 'OP10664'. The colors appearing in the photographic drawing are as true as possible with color illustrations of this type. Colors in the photographs may differ slightly from the color values cited in the detailed botanical description, which accurately describe the color of an 'OP10664' plant between 34 and 40 weeks of age.

DETAILED BOTANICAL DESCRIPTION

Figure 1:
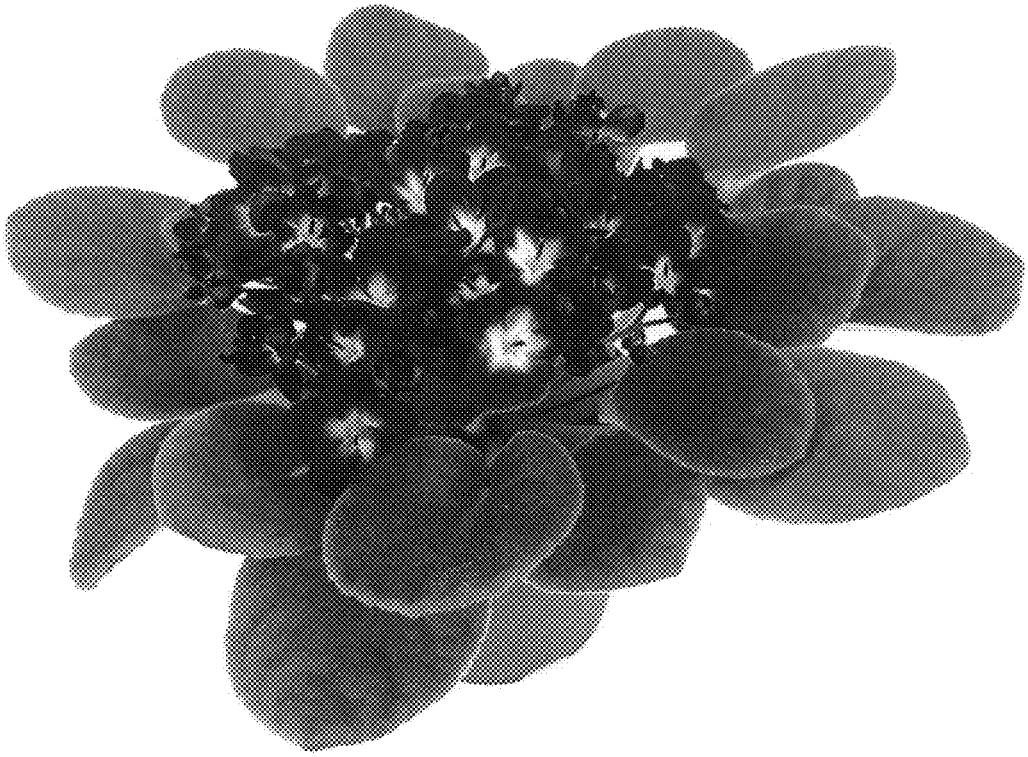
FIG. 1—Illustrates a typical 'OP10664' plant.
Figure 2:
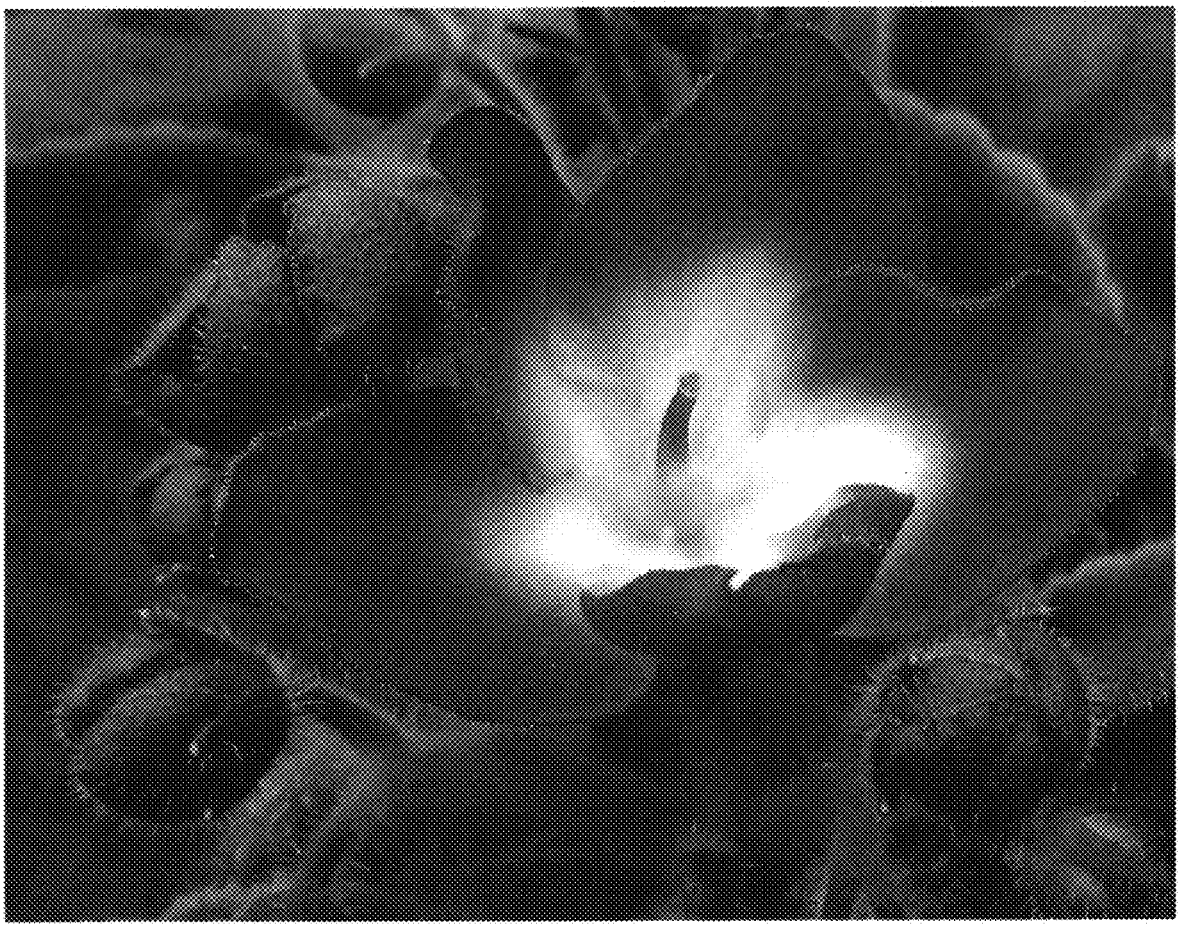
FIG. 2—Illustrates the filantherless characteristic of 'OP10664'.
Figure 3:
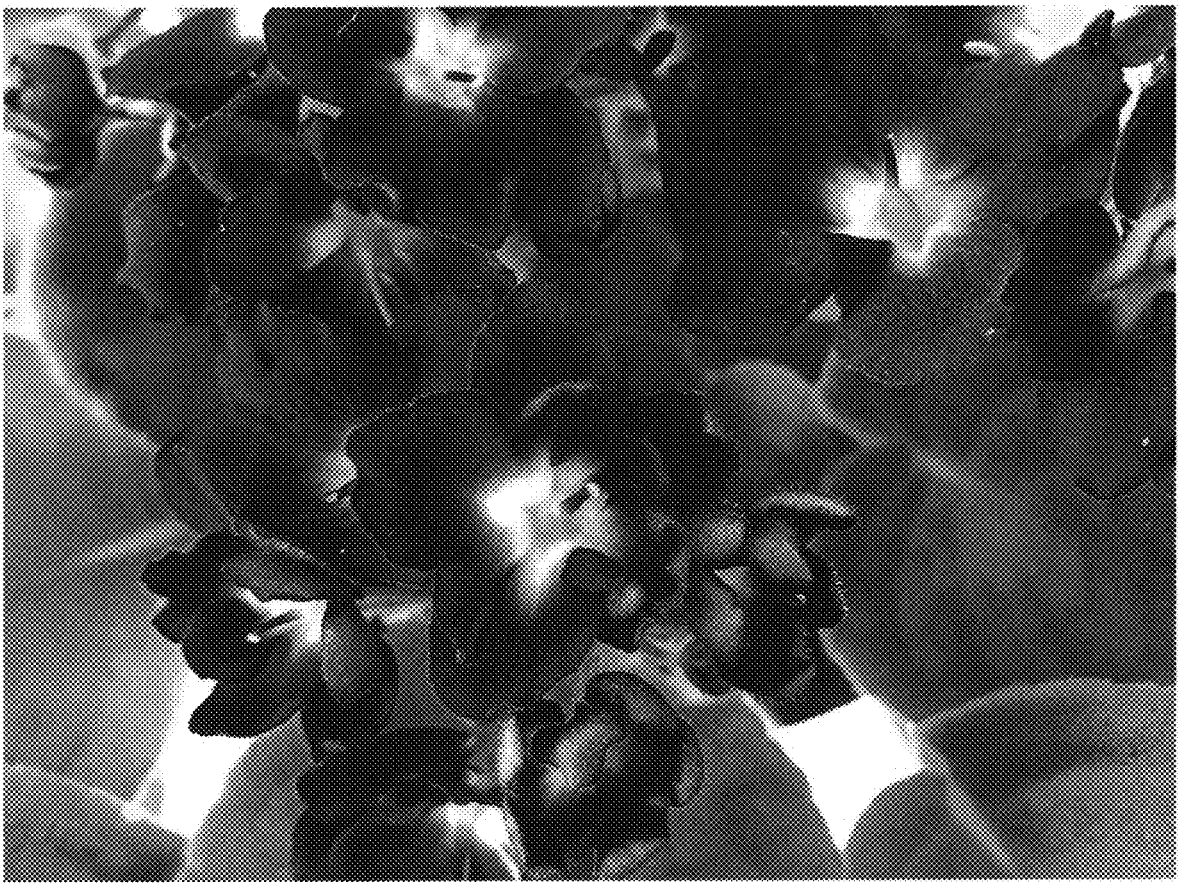
FIG. 3—Illustrates typical flowers of 'OP10664'.

In the following description, color references are made to The Royal Horticultural Society Colour Chart (R.H.S.), 1966 edition, except where general colors of ordinary significance are referred to. Color values were taken under natural sunlight conditions at approximately 12 p.m. in Nashville, Tenn.

Botanical classification: *Saintpaulia ionantha*, Ramat., c.v. 'OP10664'.

Parentage:

*Male parent.*—'5027/hbl KS *'.

*Female parent.*—'5027/20 Flied'.

Propagation: Leaf cuttings.

Plant: 12 cm to 15 cm tall when grown in pots, and 24-30 cm in diameter when fully grown. The plant is 20 to 25 cm in width horizontally across the outer perimeter of leaf span.

*Leaves.*—General form: round to oval. Size: 60-70 mm wide and 75-85 mm long. Texture: Leathery. Aspect: very slightly serrated, hairy, shiny. Shape: Oval with a rounded base and with a very slightly pointed apex. Leaves are minimally serrated. Average number of leaves: 20-24 per plant. Venation pattern: that of a regular African violet leaf. Veins: Upperside: visible; underside: well pronounced, light green, RHS Greyed-Green 194 B with occasionally purplish red RHS Greyed-Purple 186 C, shiny. Color (upperside): Yellow-green RHS 147 A-147 B. Color (underside): Greyed-green RHS 194 B to 194 C. Petiole: Strong, hairy. The color is from the yellow-green RHS 146C to 146D, while some parts hint of a fine hue 20-30% screen of greyed-purple RHS 185C. Petiole length: 45-50 mm. Petiole diameter: 2-3 mm at base, 1 mm at top. Leaf arrangement: Arranged in a basal cluster at the base of the plants with long petioles. The leaves fan out, framing the center flower cluster in a typical African Violet pattern.

*Flowers.*—Inflorescence Diameter: 32-36 mm. Inflorescence Height: 32-36 mm. Buds: Round to bell-shaped, purplish blue RHS 88A, 5-7 mm in diameter and 6-8 mm in height just before opening. Number of Sepals: Five (5). Sepal Color: At the base, minimal greenish RHS Yellow-Green 147 C with the tips RHS Greyed-Orange 177 A. The underside is RHS Greyed-Orange 177A. Sepal measurements: 4 mm long and 1 mm wide. Calyx: Shape: Funnel-shaped. Aspect: Spear-shaped, hairy. Peduncle: Character: Strong upright, hairy. Color: RHS Yellow-Green 147 C. Peduncle length: 40-45 mm. Peduncle diameter: 1-1.5 mm at base, 0.5-1 mm at top.

*Individual flowers.*—Size: 30-36 mm in diameter. Shape: Single violet-shaped with additional occasional 1-3 very small petals. Color (upperside): White center with edge being Violet RHS 89 A and RHS 89 B. Under cooler temperatures and more intensive lighting, the purplish blue edge tends to intensify and be wider. Color (underside): Between Violet RHS 85 A to RHS 85 B and Purple Violet RHS 82 C. Petals: single, violet-shaped with all petals almost equal in size with the apex slightly pointed. The texture is soft and velvety. Borne: Each of the 8-12 flower stems carries 10-14 flowers on strong, upright peduncles that are free standing above the leaves, thereby forming a compact bouquet. Flowering habit: Flowers 12-13 weeks after potting. Bloom time: Under ideal growing conditions, starting as early as week 30 and the flower remains 8 to 14 weeks from beginning of flowering. Fragrance: None.

*Reproductive organs.*—Stamens: non existent. Filaments: non existent. Pollen Color: n/a. Styles: 6-7 mm long, purplish blue, base of ovary light green.

*Roots.*—Normally developed, white when young, turning slightly brownish when older.

Disease resistance: 'OP10664' aka '5050 bl w KS 15' has shown very good resistance to all major violet diseases. Due to its filantherless blooms, it is free of botrytis and thrips.

General observations: 'OP10664' is a very attractive cultivar due to its abundance of bi-color purple flowers with white center. The lack of the filament and yellow anthers makes 'OP10664' look different than standard African Violets—the flowers look somewhat like a *Hydrangea*. The filantherless characteristic as described in the U.S. Provisional Patent Application No. 62/697,792 filed Jul. 13, 2018, "Filantherless African Violet and Methods of Breeding Thereof" also has the advantage that 'OP10664' blooms longer than standard African Violets and can not be affected by thrips or botrytis. Under ideal growing conditions, the flowers develop 9-10 weeks after planting an unrooted plantlet and create a nice flower bouquet which is free-standing above the leaves. Each of the 8-12, or more, strong flower stems carries 10-14, or more, single violet-shaped flowers with 1-3 additional small petals giving it a slightly wavy look. 'OP10664' is a medium size cultivar, designed to be grown in 10 cm pot and will take 12-13 week time period from potting to finish. The profuse flower bouquet is surrounded by medium green round to oval leaves.

I claim:

1. A new and distinct cultivar of African Violet named 'OP10664', as described and illustrated herein.

* * * * *